(12) United States Patent
Molla

(10) Patent No.: US 12,258,603 B2
(45) Date of Patent: Mar. 25, 2025

(54) PURIFICATION OF SIALOOLIGOSACCHARIDES

(71) Applicant: Glycom A/S, Hørsholm (DK)

(72) Inventor: Getachew S. Molla, Hørsholm (DK)

(73) Assignee: Glycom A/S, Hørsholm (DK)

( * ) Notice: Subject to any disclaimer, the term of this patent is extended or adjusted under 35 U.S.C. 154(b) by 0 days.

(21) Appl. No.: 18/550,209

(22) PCT Filed: Mar. 11, 2022

(86) PCT No.: PCT/IB2022/052207
§ 371 (c)(1),
(2) Date: Sep. 12, 2023

(87) PCT Pub. No.: WO2022/190055
PCT Pub. Date: Sep. 15, 2022

(65) Prior Publication Data
US 2024/0043889 A1     Feb. 8, 2024

(30) Foreign Application Priority Data

Mar. 12, 2021 (DK) .................... PA 2021 00260

(51) Int. Cl.
| | | |
|---|---|---|
| C07H 1/06 | (2006.01) | |
| C07H 1/08 | (2006.01) | |
| C12N 9/10 | (2006.01) | |
| C12P 19/04 | (2006.01) | |

(52) U.S. Cl.
CPC ............. *C12P 19/04* (2013.01); *C07H 1/08* (2013.01); *C12N 9/1048* (2013.01); *C12Y 204/00* (2013.01)

(58) Field of Classification Search
CPC ...... C07H 1/06; B01D 61/145; B01D 15/363; B01D 15/361; B01D 15/362
USPC ....................................... 536/127
See application file for complete search history.

(56) References Cited

U.S. PATENT DOCUMENTS

| | | |
|---|---|---|
| 2018/0118855 A1 | 5/2018 | Chassagne et al. |
| 2019/0031698 A1 | 1/2019 | Matwiejuk et al. |

FOREIGN PATENT DOCUMENTS

| | | |
|---|---|---|
| DK | 181061 B1 | 10/2022 |
| EP | 2408794 A2 | 1/2012 |
| EP | 3456836 A1 | 3/2019 |
| JP | H11180993 A | 7/1999 |
| JP | 2001095487 A | 4/2001 |
| JP | 2020046295 A | 3/2020 |
| WO | 2007101862 A1 | 9/2007 |
| WO | 2009113861 A2 | 9/2009 |
| WO | 2010106320 A2 | 9/2010 |
| WO | 2010116317 A1 | 10/2010 |
| WO | 2017152918 A1 | 9/2017 |
| WO | 2019043029 A1 | 3/2019 |
| WO | 2020097568 A2 | 5/2020 |

OTHER PUBLICATIONS

International Search Report and Written Opinion for International Application No. PCT/IB2022/052207, mailed May 9, 2022, 11 pages.
First technical examination of your patent application for Denmark Application No. PA202100260, mailed Sep. 10, 2021, 12 pages.
Reply to First technical examination of your patent application for Denmark Application No. PA202100260, dated Jan. 7, 2022, 2 pages.
English Translation of Allowed Claims for Denmark Application No. PA202100260, allowed Oct. 31, 2022, 2 pages.
Amendments to second technical examination of your patent application for Denmark Application No. PA202100260, mailed Oct. 31, 2022, 3 pages.
Dowex 66: Ion Exchange Resin for Sweetener Applications. Retrieved from https://www.lenntech.com/Data-sheets/Dowex-66-L.pdf (Year: 2016).

*Primary Examiner* — Robert B Mondesi
*Assistant Examiner* — Mohammad Y Meah
(74) *Attorney, Agent, or Firm* — Neal, Gerber & Eisenberg LLP

(57) ABSTRACT

The present invention relates to the isolation and purification of sialylated oligosaccharides from an aqueous medium in which they are produced.

15 Claims, No Drawings

PURIFICATION OF SIALOOLIGOSACCHARIDES

CROSS-REFERENCE TO RELATED APPLICATIONS

This application is a national stage entry pursuant to 35 U.S.C. § 371 of International Patent Application No. PCT/IB2022/052207, filed on Mar. 11, 2022, which claims priority to Denmark Application No. PA 2021 00260, filed on Mar. 12, 2021, the contents of all of which are fully incorporated herein by reference.

FIELD OF THE INVENTION

The present invention relates to the isolation and purification of sialylated oligosaccharides from a fermentation broth in which they are produced by a microorganism.

BACKGROUND OF THE INVENTION

During the past decades, the interest in the preparation and commercialisation of human milk oligosaccharides (HMOs) has been increasing steadily. The importance of human milk oligosaccharides is directly linked to their unique biological activities. Sialylated human milk oligosaccharides such as disialyllacto-N-tetraose, 3'-O-sialyl-3-O-fucosyllactose, 6'-O-sialyllactose, 3'-O-sialyllactose, 6'-O-sialylated-lacto-N-neotetraose and 3'-O-sialylated-lacto-N-tetraose, are among the major components of human milk. In these sialylated human milk oligosaccharides the sialic acid residue is always linked to the 3-O- and/or 6-O-position of a terminal D-galactose or to the 6-O-position of a non-terminal GlcNAc residue via α-glycosidic linkages. Sialylated HMOs are thought to have significant health benefits for the neonate, because of their roles in supporting resistance to pathogens, gut maturation, immune function and cognitive development (ten Bruggencate et al. Nutr. Rev. 72, 377 (2014)).

Efforts to develop processes for synthesizing HMOs, including sialylated HMOs, have increased significantly in the last ten years due to their roles in numerous human biological processes. In this regard, processes have been developed for producing them by microbial fermentations, enzymatic processes, chemical syntheses, or combinations of these technologies. With regard to productivity, fermentation processes, on a lab scale, to produce 3'-SL and 6'-SL have proved to be promising.

However, to isolate sialylated lactoses or sialylated oligosaccharides from a complex matrix such as a fermentation broth is a challenging task. According to the latest developments, the purification of sialyllactoses from broth typically comprises membrane filtration in combination with ion exchange chromatography, which ion exchange chromatography comprises a treatment of a sialyllactose containing solution with a strong acidic cation exchanger in $H^+$-form and a strong basic anion exchanger in $Cl^-$-form (see e.g. EP-A-3456836, WO 2019/043029, WO 2019/110803, WO 2019/229118).

The drawback of application of strong basic anion exchanger is that the counterion of the resin is released to the eluate. Therefore, the pH of the eluate shall be set to the required value and/or the so-produced inorganic salt(s) shall be removed in a subsequent step (e.g. by nanofiltration).

Thus, an economical way for isolating and purifying sialooligosaccharides, preferably sialyllactose, from aqueous media such as a fermentation broth on an industrial scale have been sought wherein the ion exchange resin treatment directly provides the sialooligosaccharide in the required purity/assay while a high recovery yield is maintained.

SUMMARY OF THE INVENTION

The invention relates to a method for purifying a sialylated oligosaccharide from an aqueous solution, the aqueous solution is or stemming from a fermentation broth or an enzymatic reaction mixture containing said sialylated oligosaccharide, comprising a treatment of said aqueous solution with an ion exchange resin, wherein the ion exchange treatment comprises contacting the aqueous solution containing the sialylated oligosaccharide with a strong acidic cation exchange resin in $H^+$-form followed by a weakly basic anion exchange resin in free base form, and wherein an inorganic anion of a strong acid is added to the aqueous medium containing the sialylated oligosaccharide prior to said ion exchange treatment, preferably in an amount that is around one-two molar equivalents to the binding capacity of the weakly basic anion exchange resin in free base form with respect to the sialylated oligosaccharide.

Accordingly, the invention relates to a method or process for separating a sialylated oligosaccharide/sialylated lactose from an aqueous solution, the method comprising treating said aqueous solution containing said sialylated oligosaccharide/sialylated lactose with a strong acidic cation exchange resin in $H^+$-form followed by a weakly basic anion exchange resin in free base form, wherein the aqueous solution further comprise an inorganic anion of a strong acid which is added to the aqueous solution before the resin treatment, preferably chloride, e.g. in the form of NaCl, preferably in a given amount. Moreover, the invention relates to a method or process for separating a sialylated oligosaccharide/sialylated lactose from an aqueous solution, the method comprising pre-treating an aqueous medium comprising a fermentation broth or an enzymatic reaction mixture e.g. via ultrafiltration, nanofiltration, active charcoal treatment, or any combination thereof, to result in an aqueous solution containing said sialylated oligosaccharide, and treating the aqueous solution with a strong acidic cation exchange resin in $H^+$-form followed by a weakly basic anion exchange resin in free base form, wherein the aqueous medium further comprise a co-added inorganic anion of a strong acid, preferably chloride, e.g. in the form of NaCl, in a given amount.

In one embodiment, the separation/purification method further comprises a step of ultrafiltration (UF), preferably to separate biomass and or enzymes from the aqueous medium, nanofiltration (NF), preferably to concentrate the sialylated oligosaccharide in the pre-treated aqueous medium and/or reduce an inorganic salt content of the pre-treated aqueous medium and/or separate low molecular weight organic compounds like monosaccharides or lactose from the sialylated oligosaccharide in the pre-treated aqueous medium, and/or activated charcoal (AC) treatment, preferably to decolorize the optionally pre-treated aqueous medium.

Preferably, the UF step is performed before any of the NF and AC steps and the ion exchange resin treatment. The sialylated oligosaccharide can be collected after the ion exchange resin treatment.

Also preferably, the aqueous medium is a fermentation broth of culturing a genetically modified microorganism capable of producing said sialylated oligosaccharide from an internalized carbohydrate precursor.

Also preferably, the method is carried out, applied on an aqueous medium containing a sialylated oligosaccharide, in the following sequence: UF step, NF step, optional AC treatment and treatment with a strong acidic cation exchange resin in H$^+$-form followed by a weakly basic anion exchange resin in free base form, wherein the aqueous medium further comprise a co-added inorganic anion of a strong acid, preferably chloride, e.g. NaCl, in a given amount.

One embodiment of the invention relates to a method for separating and purifying a sialylated oligosaccharide from a fermentation broth, wherein said sialylated oligosaccharide is produced by culturing a genetically modified microorganism capable of producing said sialylated oligosaccharide from an internalized carbohydrate precursor, comprising the steps of:
  a) ultrafiltration (UF) of the fermentation broth and collecting the UF permeate (UFP),
  b) nanofiltration (NF) of the UFP and collecting the NF retentate (NFR),
  c) optionally, treating the UFP and/or NFR with activated charcoal, and collecting the charcoal eluate (CE),
  d) adding an inorganic anion of a strong acid, preferably chloride, e.g. NaCl, in a given amount, to the NFR or CE, and
  e) treating the aqueous solution obtained in step d) with a strong acidic cation exchange resin in H$^+$-form followed by a weakly basic anion exchange resin in free base.

Preferably, the steps are conducted in the following order: step a), step b), optional step c), step d), step e).

Preferably, the sialylated oligosaccharide comprises only one sialyl moiety in its structure (may also be referred to as a monosialylated oligosaccharide).

Preferably, the sialylated oligosaccharide is an acidic human milk oligosaccharide (HMO) (may also be referred to as sialylated HMO).

Preferably, the sialylated HMO comprises only one sialyl moiety in its structure (may also be referred to as monosialylated HMO).

Preferably, the monosialylated HMO is a sialyllactose, e.g. 3'-SL or 6'-SL.

DETAILED DESCRIPTION OF THE INVENTION

In accordance with this invention, the term "sialylated oligosaccharide" preferably means a sugar polymer containing at least two monosaccharide units, at least one of which is a sialyl (N-acetylneuraminyl) moiety. The sialylated oligosaccharide can have a linear or branched structure containing monosaccharide units that are linked to each other by interglycosidic linkage. Advantageously, the sialylated oligosaccharide is an acidic human milk oligosaccharide.

The term "acidic human milk oligosaccharide", "acidic HMO" or "sialyl HMO" preferably means a complex sialylated oligosaccharide found in human breast milk (Urashima et al.: *Milk Oligosaccharides*. Nova Science Publishers, 2011; Chen *Adv. Carbohydr. Chem. Biochem.* 72, 113 (2015)) comprising a core structure being a lactose unit at the reducing end that can be elongated by one or more β-N-acetyl-lactosaminyl and/or one or more β-lacto-N-biosyl units, and which core structure is substituted by an α-N-acetyl-neuraminyl (sialyl) moiety and optionally can be substituted by an α L-fucopyranosyl moiety. In this regard, the acidic HMOs have at least one sialyl residue in their structure. Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DS-LNT). The term "sialylated lactose" preferably denotes 3'-SL or 6'-SL.

The term "genetically modified cell" or "genetically modified microorganism" preferably means a cell or a microorganism, such as a bacterial cell, e.g. an *E. coli* cell, in which there is at least one alteration in its DNA sequence. The alteration can result in a change in the original characteristics of the wild type cell, e.g. the modified cell is able to perform additional chemical transformation due to the introduced new genetic material that encodes the expression of an enzymes not being in the wild type cell, or is not able to carry out transformation like degradation due to removal of gene/genes (knockout). A genetically modified cell can be produced in a conventional manner by genetic engineering techniques that are well-known to those skilled in the art.

The term "genetically modified cell or microorganism capable of producing a sialylated oligosaccharide from an internalized carbohydrate precursor" preferably means a cell or a microorganism which is genetically manipulated (vide supra) to comprise a recombinant gene encoding a sialyl transferase necessary for the synthesis of said sialylated oligosaccharide, a biosynthetic pathway to produce a sialic acid nucleotide donor suitable to be transferred by said glycosyl transferase to a carbohydrate precursor (acceptor) and/or a mechanism of internalization of a carbohydrate precursor (acceptor) from the culture medium into the cell where it is sialylated to produce the sialylated oligosaccharide of interest.

The term "aqueous medium containing a sialylated oligosaccharide" preferably means an aqueous reaction or production mixture in which said sialylated oligosaccharide is produced or synthesized, and said aqueous reaction or production mixture is obtained at the end of the reaction or production. Such an aqueous medium is typically a fermentation broth or an ex vivo enzymatic reaction mixture. Accordingly, the aqueous medium usually contains—besides the sialylated oligosaccharide as primary product—by-products of different kinds, unreacted reactants or reagents, intermediates, catalysts, additives, solvents (other than water), etc., depending on the nature of the synthesis reaction or the production method.

The term "aqueous solution containing a sialylated oligosaccharide" preferably means an optionally pre-treated aqueous medium containing said sialylated oligosaccharide (vide supra) that is subjected to ion exchange resin treatment according to this invention. In this regard, the aqueous medium containing a sialylated oligosaccharide can either be directly subjected to ion exchange resin treatment according to the present invention, or that aqueous medium is pre-treated by one or more steps that are usually different than ion exchange treatment before applying the ion exchange resin treatment according to the present invention. In the sense of the above definition, the term "aqueous solution containing a sialylated oligosaccharide" embraces an aqueous medium containing said sialylated oligosaccharide and the pre-treated aqueous medium containing said sialylated oligosaccharide. By way of pre-treatment, the aqueous medium is partially purified so that the amounts of some contaminants are reduced.

The term "around" means, in one embodiment, ±10% deviation from the value indicated, or in another embodiment, ±5% deviation.

To overcome the prior art problem specified above, the present inventors modified the prior art process so that the strong basic anion exchange resin is substituted with a weakly basic anion exchange to remove various types of ionic impurities such as inorganics, proteins, amino acids etc.

Weakly basic anion exchange resins typically contain base groups having a lone pair of electrons to attract proton, such as certain nitrogen containing groups which include e.g. a primary amine, a secondary amine, a tertiary amine (free amine groups), a guanidino or a nitrogen containing heteroaromatic group (like pyridino, pyrimidino, etc.), preferably a tertiary amine. In free base form, the base groups are not in protonated form, with other words, a counteranion is absent from the base groups. Therefore, this group is able to adsorb an acid as a whole, i.e. both acid cation ($H^+$) and acid anion ($X^-$) are removed from the feed solution without ion-exchange (without releasing a counter-ion). Therefore, an ion exchanger treatment with a strong acidic cation exchanger in $H^+$-form followed by a weakly basic anion exchanger in free base form can directly provide a solution with practically no salts therein, thus without further need of purification/desalination.

In this regard, replacing the strong basic anion exchange resin with a weakly basic anionic resin seems to be a good option. Moreover, the regeneration of weakly basic anionic resins is easier and cheaper than that of a strong basic anion exchanger. The present inventors found, however, that a weak anionic resin tends to bind a higher amount of sialylated oligosaccharides/sialyllactose than a strong basic anion exchanger in $Cl^-$-form, therefore the overall recovery yield of the sialylated oligosaccharides/sialyllactose may be cca. 10-15% lower.

The present inventors surprisingly found a process/method that combines the advantageous effects associated with the application of a weakly basic anion exchange resin in free base form with the prior art high recovery yield. In this regard, it is provided a method for purifying a sialylated oligosaccharide from an aqueous solution, the aqueous solution is or stems from a fermentation broth or an enzymatic reaction mixture containing said sialylated oligosaccharide that is optionally pre-treated, comprising a treatment of said aqueous solution with an ion exchange resin, wherein
  the ion exchange treatment comprises contacting the aqueous solution containing the sialylated oligosaccharide with a strong acidic cation exchange resin in $H^+$-form followed by a weakly basic anion exchange resin in free base form, and wherein
  an inorganic anion of a strong acid, preferably chloride, e.g. NaCl, is added to the aqueous solution containing the sialylated oligosaccharide prior to the resin treatment.

In one embodiment, an amount of the added anion is around one-two molar equivalents to the binding capacity of the weakly basic anion exchange resin in free base form with respect to the sialylated oligosaccharide.

The invention thus relates to a method for purifying a sialylated oligosaccharide/sialylated lactose from other compounds present in an aqueous solution, e.g. in a fermentation broth obtained by culturing a genetically modified cell or microorganism capable of producing said sialylated oligosaccharide/sialylated lactose from an internalized carbohydrate precursor or in an enzymatic reaction mixture.

The method of the invention directly provides a purified solution that is highly enriched with the sialylated oligosaccharide/sialylated lactose from which solution the sialylated oligosaccharide/sialylated lactose can be obtained in high yield and with good purity, especially with very low inorganic anion content.

The aqueous solution containing the sialylated oligosaccharide/sialylated lactose and preferably obtained after fermentation or ex vivo enzymatic reaction can be directly subjected to the above disclosed ion exchange resin treatment, but preferably pre-treated before the ion exchange resin treatment as disclosed later.

Before subjecting the aqueous solution containing the sialylated oligosaccharide/sialylated lactose to ion exchange resin treatment, an anion is added to the feed. As mentioned above, weakly basic anion exchange resins have a certain binding capacity towards the sialylated oligosaccharide/sialylated lactose. Without being bound by a particular theory, the inventors think the co-anion added to the feed competitively binds to the functional group of the weakly basic anion exchange resin, therefore the sialylated oligosaccharide/sialylated lactose remains in the solution and goes through the resin without binding to it. As a consequence, the loss of the sialylated oligosaccharide/sialylated lactose on the resin can be minimized and its higher amount can be collected in the eluate.

The added co-anion is typically an anion of an inorganic acid. Exemplary anions are those of a strong inorganic acid for example chloride, bromide, iodide, sulphate, sulphite, nitrate, phosphate, hydrogen phosphate, phosphite, perchlorate, etc., preferably chloride. The co-anion may be added to the feed solution before resin treatment as acid or in its salt form, preferably in salt form. The cation of the salt of the co-anion is typically a cation of a strong inorganic base selected from the Group I and Group II ions except for $Be^{2+}$, such as sodium, potassium, lithium, calcium or magnesium ion, however cations from weak bases such as ammonium, $Al^{3+}$ or $Fe^{3+}$ can also be chosen. Preferred salts are water-soluble neutral salts, more preferably chlorides such as LiCl, NaCl, KCl, $MgCl_2$ or $CaCl_2$), especially NaCl.

Any amount of the co-added anion increases the recovery yield of the sialylated oligosaccharide/sialylated lactose after the ion exchange chromatography because the co-added anion inhibits the sialylated oligosaccharide/sialylated lactose from binding to the weakly basic anion exchange resin. Preferably, to achieve a commercially relevant recovery yield improvement, the molar amount of the co-added anion is at least 0.5 equivalents (in relationship to the charges of the anion and the sialylated oligosaccharide/sialylated lactose, respectively) to the molar amount of the bound sialylated oligosaccharide/sialylated lactose to the weakly basic anion exchange resin, such as around 0.6, 0.7, 0.8, 0.9 or 1 equivalent. The molar amount of the co-added anion in a certain equivalent means that the charge of the anion and the sialylated oligosaccharide/sialylated lactose is also taken into account and thus normalized. When the charge of the co-added anion and that of the sialylated oligosaccharide/sialylated lactose is equal, 1 equivalent means the same molar amount of the co-added anion than the molar amount of the bound sialylated oligosaccharide/sialylated lactose. In this case, for example, both the co-added anion and the sialylated oligosaccharide/sialylated lactose, respectively, monovalent (such as for chloride, bromide, iodide, nitrate or perchlorate, as well as for mono-sialylated oligosaccharide/monosialylated lactose [provided that the oligosaccharide/lactose does not contain charged moiety other than sialyl]) or divalent (such as for sulphate, as well as for disialylated oligosaccharide/disialylated lactose). When the charge of the co-added anion and that of the sialylated oligosaccharide/sialylated lactose is not equal, for example the following scenarios exist:

the co-added anion is divalent and the sialylated oligosaccharide/sialylated lactose is monovalent: 1 equivalent of co-added anion means its ½ molar amount with respect to the bound sialylated oligosaccharide/sialylated lactose;

the co-added anion is trivalent (e.g. phosphate) and the sialylated oligosaccharide/sialylated lactose is monovalent: 1 equivalent of co-added anion means its ⅓ molar amount with respect to the bound sialylated oligosaccharide/sialylated lactose;

the co-added anion is monovalent and the sialylated oligosaccharide/sialylated lactose is divalent: 1 equivalent of co-added anion means its 2-fold molar amount with respect to the bound sialylated oligosaccharide/sialylated lactose.

In one embodiment, the anion is added in an amount more than 1 equivalent, such as up to 2 equivalents, up to 3 equivalents, up to 5 equivalents or even up to 10 equivalents. However after reaching the binding capacity of the weak basic resin towards the co-anion (which is not the same value as that for the sialylated oligosaccharide/sialylated lactose), the co-anion leaks into the eluent. In this case, although the recovery yield of the sialylated oligosaccharide/sialylated lactose is still high, an additional step may be required to remove the excess co-anion from the eluate.

In this regard, according to a preferred embodiment, the molar amount of the co-added anion is set to be in the range of around 0.5 equivalents to around 3 equivalents, preferably 0.75-2.5 equivalents, such as 0.75-2, 0.75-1.5, 1-2.5, 1-2 or 1-1.5 equivalents. In this case, the recovery yield of the sialylated oligosaccharide/sialylated lactose is sufficiently highly whereas the anion does not leak to the eluate. Especially preferred range is 1-2 or 1-1.5 equivalents.

In order to determine the binding capacity of a weakly basic anion exchange resin in free base form towards the sialylated oligosaccharide/sialylated lactose, a feed solution containing the sialylated oligosaccharide/sialylated lactose is applied to the top of column filled with the weakly basic anion exchange resin in free base form, eluted with water and the eluate is collected in fraction. The binding capacity of the resin can be calculated as the initial amount of the sialylated oligosaccharide/sialylated lactose minus the amount that passes through the resin knowing the concentration and the volume of the feed solution as well as the eluate, and the volume of the resin, as shown in the experimental part below.

The strong cation exchange resin in protonated ($H^+$) form applied in the process of the present invention binds the inorganic cations present in the feed solution, as well as organic amines optionally made metabolically during the fermentation by the utilized production strain, amino acids and short peptides are efficiently bound and removed. The obtained resin eluate contains the sialylated oligosaccharide/sialylated lactose in acidic form.

Non-limiting examples of a suitable acidic cation exchange resin can be e.g. Amberlite™ IR100, Amberlite™ IR120, Amberlite™ FPC22, Dowex™ SOWX, Finex™ CS16GC, Finex™ CS13GC, Finex™ CS12GC, Finex™ CS11GC, Lewatit™ S, Diaion™ SK, Diaion™ UBK, Amberjet™ 1000, Amberjet™ 1200, Dowex™ 88.

The weakly basic anion exchanger in free base form adsorb inorganic acids as a whole and removes them from the feed solution, however does not bind the sialylated oligosaccharide/sialylated lactose. Non-limiting examples of a suitable weakly basic anion exchanger is Dowex™ 66 or Amberlite™ FPA53.

After the above disclosed steps, the so-obtained sialylated oligosaccharide/sialylated lactose solution can be spray-dried, freeze-dried or crystallized to obtain the sialylated oligosaccharide/sialylated lactose in solid form. Alternatively, the sialylated oligosaccharide/sialylated lactose may be provided in a form of a concentrated aqueous solution or syrup by removing water, e.g. by means of distillation, preferably vacuum distillation, or nanofiltration.

The method according to the present invention may further comprise other step(s) prior to applying the aqueous solution containing the sialylated oligosaccharide/sialylated lactose to the above disclosed resin set-up.

Once the sialylated oligosaccharide/sialylated lactose is produced either by fermentation or an ex vivo enzymatic process, the aqueous medium containing the sialylated oligosaccharide/sialylated lactose is preferably pre-treated before ion exchange treatment, e.g. subjected to ultrafiltration, preferably as a first step. A fermentation broth typically contains, besides the sialylated oligosaccharide/sialylated lactose produced, the biomass of the cells of the used microorganism together with proteins, protein fragments, DNA, endotoxins, biogenic amines, inorganic salts, unreacted carbohydrate acceptor such as lactose, sugar-like by-products, sialic acid, colorizing bodies, etc. An ex vivo enzymatic reaction mixture typically contains, besides the sialylated oligosaccharide/sialylated lactose produced, proteins, protein fragments, inorganic salts, unreacted carbohydrate acceptor such as lactose, sugar-like by-products, sialic acid and its precursors, etc. The ultrafiltration step is to separate (retain) the biomass and high molecular weight suspended solids from the soluble components of the aqueous medium which components pass through the ultrafiltration membrane in the permeate. This UF permeate (UFP) is an aqueous solution containing the produced sialylated oligosaccharide/sialylated lactose.

Any conventional ultrafiltration membrane can be used having a molecular weight cut-off (MWCO) range between about 1 and about 500 kDa, such as 10-250, 50-100, 200-500, 100-250, 1-100, 1-50, 10-25, 1-5 kDa, any other suitable sub-ranges (according to the supplier's specification). The membrane material can be a ceramic or made of a synthetic or natural polymer, e.g. polysulfone, polypropylene, cellulose acetate or polylactic acid. The ultrafiltration step can be applied in dead-end or cross-flow mode. This UF step may comprise more than one ultrafiltration step using membranes with different MWCO, e.g. using two ultrafiltration separations wherein the first membrane has a higher MWCO than that of the second membrane. This arrangement may provide a better separation efficacy of the higher molecular weight components of the aqueous medium. After this separation step the permeate contains materials that have a molecular weight lower than the MWCO of the second membrane, including the sialylated oligosaccharide/sialylated lactose of interest.

In one embodiment, the aqueous medium, preferably a fermentation broth, is ultrafiltered using a membrane having a MWCO of 5-30 kDa, such as 10-25, 15 or 20 kDa.

The biomass separation may be performed by centrifuging the broth instead of UF.

The pre-treatment of the aqueous medium containing the sialylated oligosaccharide/sialylated lactose may comprise a nanofiltration (NF) step. The NF step may follow the UF step or the optional step active charcoal treatment (vide infra). This nanofiltration step may advantageously be used to concentrate the previously treated aqueous medium containing the sialylated oligosaccharide/sialylated lactose and/or to remove ions, mainly monovalent ions, and organic materials having a molecular weight lower than that of the sialylated oligosaccharide\sialylated lactose, such as monosaccharides. The nanofiltration membrane has a MWCO that ensures the retention of the sialylated oligosaccharide\sialylated lactose of interest, that its MWCO is lower than that of the ultrafiltration membrane(s) used in step a), and around 25-50% of the molecular weight of the sialylated oligosaccharide/sialylated lactose. As an example, a nanofiltration membrane having a MWCO of about 150-300 Da is suitable for retaining sialylated lactose. In this regard the sialylated oligosaccharide/sialylated lactose is accumulated in the NF retentate (NFR). The nanofiltration can be combined with diafiltration with water in order to remove permeable molecules more effectively, e.g. until the conductivity of the permeate showing no or very low presence of salts.

In other aspect of nanofiltration, which is advantageously applicable for an UF permeate that contains higher amount of lactose, the membrane has a MWCO of 600-3500 Da ensuring the retention of the tri- or higher sialylated oligosaccharide/sialylated lactose and allowing at least a part of lactose to pass through the membrane, wherein the active (top) layer of the membrane is composed of polyamide, and wherein the $MgSO_4$ rejection factor on said membrane is around 20-90%, preferably 50-90%. The applied nanofiltration membrane is then tight for the tri- and higher sialylated oligosaccharide/sialylated lactose in order that it is efficiently retained. Such a membrane is disclosed in WO 2019/003133 which is incorporated herein by reference.

Pre-treatment of an aqueous medium containing a sialylated oligosaccharide/sialylated lactose may comprise a step of active charcoal (AC) treatment. The AC step may follow the UF step or NF step. The AC treatment helps to remove or at least reduce the amount of colorizing agents and/or water soluble contaminants, such as salts, if required.

A carbohydrate substance like a sialylated oligosaccharide/sialylated lactose of interest tends to be bound to the surface of charcoal particles from its aqueous solution, e.g. an aqueous solution obtained after the UF or NF step. Similarly, the colorizing agents also adsorb to the charcoal. While the carbohydrates and colour giving materials are adsorbed, water soluble materials not or weaker bound to the charcoal can be eluted with water. Changing the eluent from water to aqueous ethanol the adsorbed sialylated oligosaccharide/sialylated lactose can be easily eluted and collected in a separate fraction. The adsorbed colour giving substances would still remain adsorbed on the charcoal, thus decolourization and desalination can be achieved simultaneously. The charcoal treatment can be conducted by adding charcoal (e.g. powder, pellet or granulate) to the aqueous medium/solution of the sialylated oligosaccharide/sialylated lactose under stirring, filtering off the charcoal, re-suspending in aqueous ethanol under stirring and separating the charcoal by filtration. In higher scale purification, the aqueous solution of the sialylated oligosaccharide/sialylated lactose after the UF step and/or NF step is loaded to a column packed with charcoal, which may optionally be mixed with celite, then the column is washed with the required eluent. The fractions containing the sialylated oligosaccharide/sialylated lactose are collected. From these fractions, if necessary, the ethanol may be removed by e.g. evaporation to give an aqueous solution of the sialylated oligosaccharide/sialylated lactose.

Alternatively, under certain conditions, the sialylated oligosaccharide is not, or at least not substantially, adsorbed on the charcoal particles and elution with water gives rise to an aqueous solution of the sialylated oligosaccharide/sialylated lactose without its significant loss, meanwhile the colour giving substances remain adsorbed.

The sialylated oligosaccharide/sialylated lactose can be produced in chemical synthesis, ex vivo enzymatic synthesis or by culturing a genetically modified capable of producing a sialylated oligosaccharide/sialylated lactose. The preferred method of producing a sialylated oligosaccharide/sialylated lactose is fermentation.

For chemical synthesis of 6'-SL see e.g. WO 2010/116317 or WO 2011/100979.

For ex vivo enzymatic synthesis of sialylated lactoses by using a transsialidase see e.g. Maru et al. *Biosci. Biotech. Biochem.* 56, 1557 (1992), Masuda et al. *J. Biosci. Bioeng.* 89, 119 (2000) or WO 2012/007588. For ex vivo enzymatic synthesis of 3'-SL by using a sialyl transferase see e.g. WO 96/32492, Gilbert et al. *Nature Biotechnol.* 16, 769 (1998), WO 99/31224 or Mine et al. *J. Carbohydr. Chem.* 29, 51 (2010).

The fermentative production comprising a genetically modified cell preferably occurs in the following way. An exogenously added acceptor is internalized from the culture medium into the cell where it is converted to the sialyl oligosaccharide of interest in a reaction comprising enzymatic sialylation mediated by an appropriate sialyl transferase. In one embodiment, the internalization can take place via a passive transport mechanism during which the exogenous acceptor diffuses passively across the plasma membrane of the cell. The flow is directed by the concentration difference in the extra- and intracellular space with respect to the acceptor molecule to be internalized, which acceptor is supposed to pass from the place of higher concentration to the zone of lower concentration tending towards equilibrium. In another embodiment, the exogenous acceptor can be internalized in the cell with the aid of an active transport mechanism, during which the exogenous acceptor diffuses across the plasma membrane of the cell under the influence of a transporter protein or permease of the cell. Lactose permease (LacY) has specificity towards mono- or disaccharide selected from galactose, N-acetyl-glucosamine, a galactosylated monosaccharide (such as lactose), an N-acetyl-glucosaminylated monosaccharide and glycosidic derivatives thereof. All these carbohydrate derivatives can be easily taken up by a cell having a LacY permease by means of an active transport and accumulate in the cell before being glycosylated (WO 01/04341, Fort et al. *J. Chem. Soc., Chem. Comm.* 2558 (2005), EP-A-1911850, WO 2013/182206, WO 2014/048439). This is because the cell is able to transport these carbohydrate acceptors into the cell using its LacY permease, and the cell lacks any enzymes that could degrade these acceptors, especially LacZ. The specificity towards the sugar moiety of the substrate to be internalized can be altered by mutation by means of known recombinant DNA techniques. In a preferred embodiment, the exogenously added acceptor is lactose, and its internalization takes place via an active transport mechanism mediated by a lactose permease of the cell, more preferably LacY. Being internalized in the cell, the acceptor is sialylated by means of a sialyl transferase expressed by a heterologous gene or nucleic acid sequence which is introduced into the cell by known techniques, e.g. by integrating it into the chromosome of the cell or using an expression vector. The genetically modified cell comprises a biosynthetic pathway to produce a sialic acid monosaccharide nucleotide donor (typically CMP-sialic acid) suitable to be transferred by the corresponding sialyl transferase. The genetically modified cell can produce CMP-sialic acid, in two ways. In one way, exogenously added sialic acid is internalized actively or passively, preferably actively by a sialic acid permease, more preferably by that encoded by nanT, and subsequently converted to CMP-sialic acid by a CMP-NeuAc synthase, e.g. encoded by a heterologous neuA. In another way the internally available UDP-GlcNAc is utilized, by expressing heterologous neuC, neuB and neuA that convert it to CMP-sialic acid via ManNAc and sialic acid as intermediates. In the meantime, the cell's catabolic activity on sialic acid and its precursor is suppressed by inactivating/deletion of the aldolase gene (nanA) and/or the ManNAc kinase gene (nanK). The internalized carbohydrate precursor can be the subject of glycosylation other than sialylation, e.g. N-acetyl-glucosaminylation, galactosylation and/or fucosylation before being sialylated as described above.

In a preferred embodiment of the production of a sialylated oligosaccharide/sialylated lactoses by a genetically modified microorganism, the microorganism able to produce a sialylated oligosaccharide is an *E. coli*, preferably of LacZ$^-$ or LacY$^+$LacZ$^-$ genotype carrying neuBCA. The heterologous sialyl transferase gene in the microorganism is preferably an α-2,3- or an α-2,6-sialyl transferase with the aid of which, from the exogenously added lactose as carbohydrate acceptor, 3'-SL or 6'-SL is produced, respectively. Such a microorganism is disclosed e.g. in WO 2007/101862, Fierfort et al. *J. Biotechnoi.* 134, 261 (2008), Drouillard et al. *Carbohydr. Res.* 345, 1394 (2010) or WO 2017/101958.

Accordingly, one embodiment of the present invention is a method for purifying a sialylated lactose from a fermentation broth obtained by culturing a genetically modified microorganism capable of producing said sialylated lactose from an internalized lactose, comprising the steps of:
  i) ultrafiltration of the broth to obtain an ultrafiltration permeate,
  ii) nanofiltration of the ultrafiltration permeate to obtain a nanofiltration retentate,
  iii) optionally, activated charcoal treatment of the nanofiltration retentate to obtain a decolorized aqueous solution,
  iv) adding an anion to the solution obtained in step ii) or iii),
  v) treatment of the aqueous solution obtained in step iv) with a strong cation exchange resin in H$^+$-form, and
  vi) treatment of the eluate of step v) with a weakly basic anion exchange resin in free base form and collecting the eluate.

Preferably, a pre-determined amount of co-anion is added in step iv). More preferably, the amount of the co-anion is 0.5-3 equivalents (in relationship to the charges of the anion and the sialylated lactose, respectively) to the molar amount of the bound sialylated lactose to the weakly basic anion exchange resin.

EXAMPLES

Production of 6'-SL

6'-SL was produced by fermentation using *E. coli* of LacY$^+$LacZ$^-$ genotype having an α-2,6-sialyl transferase integrated in and expressed from its chromosome, and neuBCA and nadC expressed from the same plasmid, in accordance with WO 2017/101958. The fermentation broth was purified (UF, NF) in accordance with EP-A-3456836 to provide an aqueous solution containing 6'-SL which was used in the following examples.

Example 1

This example demonstrates the determination of the amount of 6'-SL that binds to the weakly basic resin.

The aqueous solution containing 6'-SL was passed through two interconnected columns filled with different ion exchange resins so that the eluate from resin 1 was directly led to the top of the column of resin 2. Resin 1 was Dowex™ 88 (a strongly acidic cation exchange resin (SAC) in H$^+$-form), while resin 2 was a weakly basic anion exchange resin Dowex™ 66 in free base form. To the eluate from resin 2, NaOH-solution was added to set the pH to around 5.

Three experiments were conducted parallelly, the processing operational parameters of each are summarized in the table below.

|  | #1 | #2 | #3 |
|---|---|---|---|
| volume of Dowex ™ 88 H$^+$ (l) | 0.9 | 0.9 | 0.11 |
| volume of Dowex ™ 66 free base (l) | 0.63 | 0.63 | 0.11 |
| mass of feed solution (g) | 1995 | 2285 | 483 |
| mass of 6'-SL in the feed solution (g) | 461 | 528 | 84 |
| mass of lactose in the feed solution (g) | 16 | 19 | 0.5 |
| mass of 6'-SL in the effluent after pH adjusted (g) | 367 | 424 | 68.5 |
| mass of lactose in the effluent after the pH adjusted (g) | 24 | 32 | 1.0 |
| 6'-SL yield (%) | 79.7 | 80.3 | 81.3 |
| mass of 6'-SL lost due to hydrolysis (g) | 14 | 24 | 1.0 |
| percentage of 6'-SL lost due to hydrolysis (%) | 2.9 | 4.6 | 1.2 |
| percentage of 6'-SL lost due to adsorption (%) | 17.4 | 15.1 | 17.5 |
| fraction of the lost 6'-SL due adsorption (%) | 85.5 | 76.8 | 93.6 |
| binding capacity of Dowex ™ 66 with respect of 6'-SL (mol/l of resin) | 0.20 | 0.20 | 10.21 |

Carbohydrates were determined by HPLC (ion chromatography on CarboPac PA200 with PAD).

As it is clear from the data, a significant amount of 6'-SL was lost due to its binding to the weak basic anion exchange resin, and a smaller amount via hydrolysis (calculated from the lactose balance). One litre of Dowex™ 66 (wet volume) thus binds around 0.2 mols of 6'-SL.

Example 2

The same aqueous solution of 6'-SL and the same resin set-up were used in this example with the difference that a calculated amount of NaCl was added to the resin feed. The processing operational parameters of the experiments are summarized in the table below:

|  | #4 | #5 | #6 |
|---|---|---|---|
| volume of Dowex ™ 88 H$^+$ (l) | 0.11 | 0.11 | 0.30 |
| volume of Dowex ™ 66 free base (l) | 0.11 | 0.11 | 0.21 |
| mass of feed solution (g) | 483 | 483 | 691 |
| mass of 6'-SL in the feed solution (g) | 84.2 | 84.2 | 152 |
| NaCl added to the feed solution with respect to the biding capacity of Dowex ™ 66 determined above (molar equiv.) | 0.99 | 1.55 | 10.67 |
| mass of 6'-SL in the effluent after pH adjusted (g) | 78.6 | 81.9 | 151 |
| 6'-SL yield (%) | 93.4 | 97.2 | 99.3 |

Samples from the effluents were freeze-dried and analysed with capillary electrophoresis for inorganic anion content:

|  | #4 | #5 | #6 |
|---|---|---|---|
| chloride (wt %) | 0.071 | 0.004 | 3.42 |
| sulphate (wt %) | <d.l. | <d.l. | 0.09 |
| phosphate (wt %) | <d.l. | <d.l. | <d.l. |

* < d.l.: below detection limit

The examples demonstrated that addition of 1 or 1.5 molar equivalents of NaCl to the resin feed (experiments #4 and #5, respectively) effectively enhanced the recovery yield of 6'-SL whereas the amount of the anions in the isolated samples was very low and way below the regulatory requirements. In case of adding around 10 equivalents of NaCl (experiment #6), although the recovery yield was high, substantial amount of salt contaminated the isolated 6'-SL.

Conclusion: the claimed modified purification process provides 6'-SL in at least the same yield and the same purity/assay, especially in terms of anion content, as the prior art process disclosed in EP-A-3456836.

The invention claimed is:

1. A method for purifying a sialylated oligosaccharide from an aqueous solution, the method comprises the sequential steps of:
    a) obtaining an aqueous solution comprising a sialylated oligosaccharide;
    b) adding a compound comprising an inorganic anion of a strong acid and a counter cation to the aqueous solution obtained in step a);
    c) contacting the aqueous solution obtained in step b) with a strong acidic cation exchange resin in H+ form; and
    d) contacting the aqueous solution obtained in step c) with a weakly basic anion exchange resin in free base form.

2. The method according to claim 1, wherein the inorganic anion of the compound added in step b) is chloride.

3. The method according to claim 2, wherein the compound is NaCl.

4. The method according to claim 1, wherein the inorganic anion of the compound added in step b) is added in a molar amount of at least 0.5 equivalents to the binding capacity of the weakly basic anion exchange resin with respect to the sialylated oligosaccharide.

5. The method according to claim 4, wherein the molar amount is 0.75 to 2.5 equivalents.

6. The method according to claim 5, wherein the molar amount is 1.0 to 1.5 equivalents.

7. The method according to claim 1, wherein the aqueous solution containing the sialylated oligosaccharide of step a) is an optionally pretreated aqueous medium comprising a fermentation broth or an ex vivo enzymatic reaction mixture.

8. The method according to claim 7, wherein the aqueous medium is a fermentation broth, and the pre-treatment comprises one or more of centrifugation, ultrafiltration, nanofiltration and activated charcoal treatment.

9. The method according to 8, the method comprising:
    (i) ultrafiltration (UF) of the fermentation broth and collecting the UF permeate (UFP),
    (ii) nanofiltration (NF) of the UFP and collecting the NF retentate (NFR),
    (iii) optionally, treating the UFP and/or NFR with activated charcoal, and collecting the charcoal eluate (CE),
    (iv) adding a compound comprising an inorganic anion of a strong acid and a counter cation to the NFR or CE,
    (v) contacting the aqueous solution obtained in step (iv) with a strong acidic cation exchange resin in H+-form,
    (vi) contacting the aqueous solution obtained in step v) with a weakly basic anion exchange resin in free base form.

10. The method according to claim 9, wherein the inorganic anion of the compound added in step iv) is chloride.

11. The method according to claim 1, wherein the sialylated oligosaccharide is an acidic human milk oligosaccharide (HMO).

12. The method according to claim 11, wherein the acidic HMO is selected from the group consisting of 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), 10 LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DS-LNT).

13. The method according to claim 11, wherein the acidic HMO is 3'-SL or 6'-SL.

14. The method according to claim 13, the method comprising:
    (i) culturing a genetically modified microorganism capable of producing 3'-SL or 6'-SL from an internalized lactose,
    (ii) performing ultrafiltration of the broth of step (i) to obtain an ultrafiltration permeate,
    (iii) performing nanofiltration of the ultrafiltration permeate to obtain a nanofiltration retentate,
    (iv) optionally, treating the nanofiltration retentate with activated charcoal to obtain a decolorized aqueous solution,
    (v) adding NaCl to the solution obtained in step (iii) or (iv) in a molar amount of 0.75 to 2.5 equivalents to the binding capacity of the weakly basic anion exchange resin with respect to 3'-SL or 6'-SL,
    (vi) contacting the aqueous solution obtained in step (v) with a strong cation exchange resin in H+-form, and
    (vii) contacting the eluate of step (vi) with a weakly basic anion exchange resin in free base form and collecting the eluate.

15. The method according to claim 14, wherein the molar amount in step (v) is 1.0 to 1.5 equivalents.

* * * * *